United States Patent [19]
Tanaka et al.

[11] Patent Number: 5,837,463
[45] Date of Patent: Nov. 17, 1998

[54] NUCLEIC ACID OF C TYPE HEPATITIS VIRUS DERIVATION AND PROCESS FOR DETECTION VIRUS USING SAID NUCLEIC ACID

[75] Inventors: Torahiko Tanaka; Nobuyuki Katoh; Kunitada Shimotohno, all of Tokyo, Japan

[73] Assignees: Rational Drug Design Laboratories, Fukushima; National Cancer Center, Tokyo, both of Japan

[21] Appl. No.: 731,272

[22] Filed: Oct. 11, 1996

[30] Foreign Application Priority Data

Oct. 17, 1919 [JP] Japan .................................. 7-268700

[51] Int. Cl.⁶ .............................. C12Q 1/68; C07H 21/04
[52] U.S. Cl. .......................... 435/6; 435/172.3; 536/23.1; 536/24.3
[58] Field of Search .................. 536/24.1, 24.5, 536/23.1; 435/6, 172.1, 172.3; 514/44

[56] References Cited

FOREIGN PATENT DOCUMENTS 9708310   3/1997   WIPO .

OTHER PUBLICATIONS

T. Tanaka et al., Kantansui, 32, 6, 807–812, 1996.
Proc. Natl. Acad. Sci. USA, Vol. 88 pp. 1711–1715, March 1991, Biochemistry.
IX Triennial International Symposium, Apr. 21–25 1996 Rome, Italy.
Japanese Journal of Cancer Research, 55th annual meeting Oct., 1996 Yokohama.
T. Tanaka et al., 44th Anual Meeting of Japanese Society of Virology, 1996.
Proc. Natl Sci. USA, Vol. 88, pp. 10292–10296, Nov.1991, Biochemistry.
Proc. Natl. Acad. Sci. USA, Vol. 87, pp. 9524–9528, Dec 1990, Biochemistry.
Nucleic Acids Research, 1992, Vol. 20, No. 23.
Virus Research 23 (1992) 39–53.
Virology, 190, 894–899 (1992).
Virology 189, 102–113 (1992).
Journal of General Virology (1991), 72, 2697–2704.
Gene. 120 (1992) 317–318.
Journal of Medical Virology 40:254–260 (1993).
Journal of General Virology (1994), 75 3279–3284.
Journal of General Virology (1994), 75, 1761–1768.
Journal of General Virology (1994), 75, 3623–3628.
Journal of General Virology (1994), 75, 629–635.
Journal of Virology, Jun. 1993, p. 2961–2971.
Virology 188, 331–341 (1992).
XIth International Congress of Virology, Jerusalem, Israel, 11–16 Aug. 1996.
Journal of Virology, May 1996, p. 3307–3312.
Vol. 215, No. 2, 1995, Biochemical&Biophysicaal Research Communications, Oct. 13, 1995, pp. 744–749.
Arch Virol (1994) 134: 293–302.
Journal of Hepatology, 1993; 17 (Suppl.3):S94–S107.
URNAL of Virology, Mar. 1991, pp. 1105–1113.
Gewirtz et al. PNAS 93: 3161–3163, 1996.
Rojanasakal. Adv. Drug Delivery Revs. 18 (1996) 115–131.

*Primary Examiner*—John LeGuyader
*Attorney, Agent, or Firm*—Sughrue, Mion, Zinn, Macpeak & Seas, PLLC

[57] ABSTRACT

An objective of this invention is to clarify the sequence of the 3'-end site of HCV genome and to provide a new process for detecting HCV.

A new sequence with a highly conserved 3'-end site of the HCV genome has been found. Using the said sequences, new process for detecting HCV, a process for inhibiting proliferation of HCV, etc. have been provided.

14 Claims, 1 Drawing Sheet

FIG. 1A
FIG. 1B
FIG. 1C

NUCLEIC ACID OF C TYPE HEPATITIS VIRUS DERIVATION AND PROCESS FOR DETECTION VIRUS USING SAID NUCLEIC ACID

FIELD OF THE INVENTION

This invention relates to detection and treatment of C-type hepatitis virus (hereinafter called "HCV"),

BACKGROUND OF THE INVENTION

HCV is a plus-stranded RNA virus and breeds in the human liver. The ratio of C-type hepatitis virus cases among all hepatitis cases is high and said virus is a very important virus from the viewpoint of the treatment and prevention of hepatitis. However, because the virus concentration in the blood serum of patients is low, the HCV is more difficult to study than other main viruses (for example B-type hepatitis virus, etc.).

In particular, since there is no appropriate in-vitro experimental system, the replication mechanism of the HCV genome or HCV particles which are useful for development of inhibitors has not been clarified. Hitherto, a wide variety of reports have been presented regarding various subtypes of the HCV genome([I/1a type] J. H. Han et al., Proc. Natl. Acad. Sci. USA 88, 1711–1715, 1991/G. Inchauspe et al., Proc. Natl. Acad. Sci. USA 88, 10292–10296, 1991/H. Okamoto et al., Nucleic Acid Res. 20, 6410, 1992 [II/1b type] N. Kato et al, Proc. Natl Acad. Sci. USA 87, 9524–9528, 1990/T. Tanaka et al., Virus Res. 23, 39–53, 1992/A. Takamizawa et al., J. Virol. 65, 1105–1113 1991/H Okamoto et al., Virology 190, 894–899, 1992/P. J. Chen et al., Virology 188, 102–113, 1992/M Honda et al., Gene 120, 317–318, 1992 N Hayashi et al., J. Hepatol. 17(suppl .3), S94–107, 1993/Y. Wang et al., J. Med. Virol. 40, 254–260, 1993 [III/2a type] H. Okamoto et al., J Gen. Virol. 72, 2697–2704, 1991 [IV/2b type] H. Okamoto et al., Virology 188, 311–341, 1992 [V/3a type] N. Yamada et al., J Gen. Virol. 75, 3279–3284, 1994/M Sakamoto et al., J. Gen.Virol. 75, 1761–1768, 1994 [VI/3b type] K. Chayama et al., J. Gen Virol, 75, 3623–3628, 1994 [1c type] H. Okamoto et al., J. Gen Virol. 75, 629–635, 1994). However, in regard to the sequence of the genome 3'-end, which is believed to be the initiation site of the genomic replication, no definite finding has been obtained to date in spite of the fact that this area is believed to play the most important role in replication.

SUMMARY OF THE INVENTION

This invention has been made to clarify the sequence of 3'-end of HCV genome and to provide a new HCV detection method, etc.

DETAILED DESCRIPTION OF THE INVENTION

The inventors carried out reverse transcription reaction with the 3'-end of HCV genome protected and cloned cDNA which corresponds to HCV genome 3'-end area RNA in order to confirm the sequence in the 3'-end portion of the HCV genome. It has been an established theory that the 3'-end of HCV genome ends with the U cluster, but surprisingly, the inventors have newly discovered that another sequence (hereinafter called the "sequence 3'X") exists downstream of the said U cluster, and completed this invention. By analyzing clinical samples, the inventors have found that the said "sequence 3'X" is specific to HCV, that it exists not only in II/1b type (former Japanese type) but also other HCV types (III/2a type, which is distributed around the world but is the second most frequently detected type in Japan and is located farthest in terms of heredity from the II/1b type of HCV types presently known) and said "sequence 3'X" is highly conserved between clones, and have the inventors confirmed that the "sequence 3'X" is very useful for the detection of HCV and the suppression of its proliferation.

Specifically, the present invention relates to double-stranded DNA comprising single-stranded DNA which specifically hybridizes the whole or a part of the sequence of "SEQ ID NO:2" or that strand complementary to the said sequence in addition to the said single-stranded DNA and its complementary strand.

This invention also relates to double-stranded DNA comprising single-stranded DNA for specifically hybridizing the whole or a part of the "SEQ ID NO:4" sequence or that complementary to the said sequence in addition to the said single-stranded DNA and its complementary stranded.

This invention relates to the primer comprising the said single-stranded DNA and to the kit to detect HCV by using the said primers as well as to the method for detecting C-type hepatitis virus including the process to carry out PCR on the sample using the said primer.

In addition, the present invention relates to a C-type hepatitis proliferation inhibitor comprising the said single-stranded DNA.

It is possible to confirm the existence of HCV in the sample by detecting the existence of nucleic acid having the "Sequence 3'X" in the sample. In particular, because the "Sequence 3'X" is a sequence which is exceptionally highly conserved in HCV with many variations, it is assumed that the inspection utilizing the "Sequence 3'X" is highly reliable.

For detection of the existence of nucleic acid having the "Sequence 3'X" in the sample, several methods exists, including observation of a hybridization between nucleic acid having the "Sequence 3'X" in the sample and oligo-nucleotide probe which specifically hybridizes the "Sequence 3'X," and observation of the amplification of the "Sequence 3'X" by the PCR technique using a primer which specifically hybridizes the "Sequence 3'X," etc. However it is assumed that the PCR technique is the most suitable in terms of sensitivity and convenience.

Because the HCV gene is RNA, the viral RNA must be converted to DNA by a reverse transcription reaction prior to PCR. Consequently, the RT-PCR technique is used. Any primer which specifically hybridizes the "Sequence 3'X" can be used, but those which are highly homologous to the "Sequence 3'X" and have length of about 20 residues are most suitably used. It is preferable to use an area which is free from variation between clones (for example, those illustrated in Table 2 or Table 3. In general, the vicinity of the 3'-end of RNA virus genome forms a specific secondary structure and is assumed to be an area essential for the virus to start proliferation (Jacobson, S. J. et al., J. Virol. 67, 2961,(1993)). Similarly, it is also assumed that the "Sequence 3'X" of HCV is an area essential for the virus to start proliferation. Consequently, it may be said that if the "Sequence 3'X" exists in the sample, there is a high possibility that the HCV in the sample possesses active multiplication capabilities and the existence of the "Sequence 3'X" serves as an index of progress of hepatitis and may be able to be used for early diagnosis of aggravation of hepatitis.

Because it is assumed that the "Sequence 3'X" is an area essential for virus proliferation, it is assumed that is may be possible to effectively inhibit proliferation of HCV by inhibiting the functions of the "Sequence 3'X" portion. Specifically, an antisense oligomer for the "Sequence 3'X" should be effective for suppressing proliferation of HCV. The said antisense oligomer may be any type if it specifically hybridizes the "Sequence 3'X." However, oligomers which are highly homologous to the "Sequence 3'X" and have the length of 15–20 nucleotides are most suitable. The antisense oligomer used for suppressing proliferation of HCV can be chemically modified to prevent degradation in vivo. Examples of the specific chemical modification method include a process for replacing the phosphate group that forms phosphodiester with the methyl group (Smith. C. et al., Proc. Natl. Acad. Sci. USA, 83, 2787 (1986)), etc. or a process for replacing O-atom of phosphate group with S-atom (Matsukura. M. et al., Proc. Natl. Acad. Sci. USA, 84, 7706 (1987)). In addition, the ribozyme which specifically cuts the "Sequence 3'X" and the chemicals which inhibit the association between the "Sequence 3'X" and HCV protein are assumed to be effective to inhibit the capabilities of the "Sequence 3'X." Examples of candidates of HCV protein which can associate with the "Sequence 3'X" are NS5B (RNA replicase), NS3 (RNA helicase), etc.

In addition, in developing the inhibitor of HCV, it is important to clarify the virus life cycle. In this event, if an experimental system is established in which HCV can be produced by administering the HCV genome to the cell (or cell-free system), a majority of the HCV replication mechanism may be clarified, but presently, an attempt to establish an experimental system has not yet succeeded. This may be primarily attributed to the fact that the experiments are being carried out in the HCV construct lacking the "Sequence 3'X" under the mistaken belief that it is the whole-length genome. Consequently, the actual whole-length genome, i.e., that which contains the "Sequence 3'X" which is believed to play an important role for replication, is assumed to be greatly useful for developing and establishing the replication system. Specifically, consideration is given to establishing a system for detecting the synthesis of a minus strand by introducing the whole sequence of the HCV genome containing the "Sequence 3'X" into the cell or a system in which the minus strand synthesis is detected by observing the activity of reporter gene that is located upstream of the "Sequence 3'X" with reverse direction.

BRIEF DESCRIPTION OF THE DRAWING

FIG. 1A shows synthesis of cDNA to HCV RNA minus strand in liver cells (by RT reaction).

FIG. 1B shows the addition of dC tail to the 3'-end of cDNA (terminal transferase reaction).

FIG. 1C shows the anchor PCR process.

EXAMPLES

Referring now to the examples, the present invention will be described in further detail hereinafter. However, it is to be understood that the invention is not intended to be limited to these examples.

[Example 1] Extraction of RNA Containing HCV RNA Genome From Heptocyte

The whole RNA fraction was recovered from non-cancer portion (about 0.5 g) of resected sample of liver cancer operation using an RNA extraction kit (RNAzo1B/registered mark: BiotecxLaboratories). The recovered RNA was dispensed to a microtube, and were allowed to precipitate with ethanol. Thereafter, the sediments were suspended in 75% ethanol and stored at −70° C. The HCV used was the II/1b type which is the most frequently observed in Japan.

[Example 2] Modification of 3'-end of RNA

In the reverse transcription PCR for synthesizing DNA using the recovered RNA as a template (hereinafter called "RT-PCR"), sometimes non-specific reactions such as self-priming reactions, etc. occur in which synthesis takes place with template RNA as a primer. In order to inhibit such reactions, the 3'-end was modified so that polymerase does not act on the template RNA in the PCR. This 3'-end modification was carried out in the following manner in conformity to the technique advocated by Gunji et al. (Arch. Virol., 1994, 134; 293–302).

After RNA (about 20 μg/180 μl) of Example 1 was heated for 10 minutes at 80° C., it was cooled on ice. Than, 20 μl of 0.5M sodium acetate (pH 5.0) and then 50 μl of 20 mM $NaIO_4$ were added, and the solution was incubated in darkness for 12 hours at 30° C. After adding 60 μl of 10% ethylene glycol to this reaction solution, and RNA was precipitated with ethanol. RNA as precipitate residue was dissolved in 300 μl of water. Then, 100 μl of 0.1M $NaBH_4$ dissolved in 0.05N NaOH were added and allowed to react in darkness for 1 hour at 0° C., and after adding to this reaction solution 30 μl of 50% acetic acid, RNA was precipitated with ethanol.

[Example 3] Synthesis of cDNA by Reverse Transcription Reaction (Reverse Transcription Reaction)

As shown in FIG. 1A, cDNA was synthesized from RNA by reverse transcription reaction. This reverse transcription reaction was carried out as follows. Five pieces of reaction tube containing the reaction liquid of the following composition were prepared: 4.0 μl of the "1st strand buffer with five-fold concentration," 4.0 μl of dNTP (2.5 mM each), 1.0 μl of 0.1 MDTT, 2.0 μl of "primer 1" (10 μM), 1.5 μl of the said RNA (1 μg/μl), and 6.5 μl of water. The "1st strand buffer with five-fold concentration" (available from GIBCO BRL Company) is composed of 250 mM Tris-HCl (pH 8.3), 375 mM KCl , and 15 mM $MgCl_2$. The said "primer 1" has the sequence 5'-TACTCCTACTCTCTGTAGGG-3' (SEQ ID NO:5) which corresponds to the 9325–9344 base in the HCV-JT base (Tanaka et al., Virus. Res. 23. 39–53 (1992)). The said reaction tubes were heated for 3 minutes at 90° C., and then rapidly cooled in ice water to denature the RNA. Then, 1 μl of the reverse transcriptase (Superscript II, available from GIBCO BRL Company) was added to each tube, and cDNA synthesis reaction was allowed to take place for 60 minutes at 65° C. To the reaction solution of each tube, 1.4 μl of 6N NaOH were added and heated for 30 minutes at 65° C. to hydrolyze RNA, and the reaction solution in these five tubes were recovered into one tube, to which 7.0 μl of 6N acetic acid were added for neutralization. In addition, 2.0 μl of 6N acetic acid were added to adjust the pH to 5 and then, precipitation with ethanol was carried out. The precipitate residue cDNA was dissolved in 25 mM Tris-HCl (pH 7.4) and purified using the DNA purification kit "GENOBIND (available from CLONTECH Company)." After cDNA obtained was allowed to undergo ethanol precipitation, the precipitate residue was dissolved in 8 μl of water.

[Example 4] Anchor PCR Process (dC tailing)

Figures 1A, 1B:
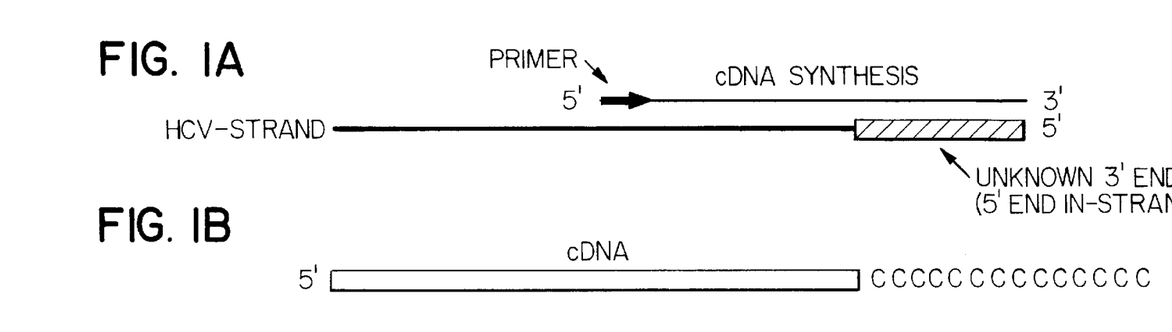

As shown in FIG. 1B, poly C tail was added to the 3'-end of cDNA synthesized in the above Example. The dC-tailing reaction was carried out as follows.

The dC tailing reaction liquid is composed of the following. 6.0 μl of the five-fold concentration TdT buffer, 6.0 μl of 2.5 mM dCTP, 4.0 μl of cDNA obtained in Example 2, 0.3 μl of 0.1M DTT, and 11.7 μl of water. Now the "five-fold concentration TdT buffer is composed of 0.5M sodium cacodylate (pH 7.0), 10 mM $MnCl_2$ and 0.5M DTT. This reaction liquid was put into a tube, cooled on ice after heating for 3 minutes at 98° C. to denature cDNA; then, 2.0 μl of terminal deoxynucleotidyl transferase (available from Toyobo Company) were added, and the liquid was allowed to react for 1 hour at 37° C. and poly C tail was added.

The reaction liquid was treated with phenol/chloroform and underwent ethanol precipitation twice (for the auxiliary salt of precipitation, ammonium acetate was used for the first time and sodium acetate for the second time), and the precipitate residue, cDNA with poly C tail added, was dissolved in 8 μl of water.

[Example 5] Anchor PCR Process (Amplification Reaction)

Figure 1C:
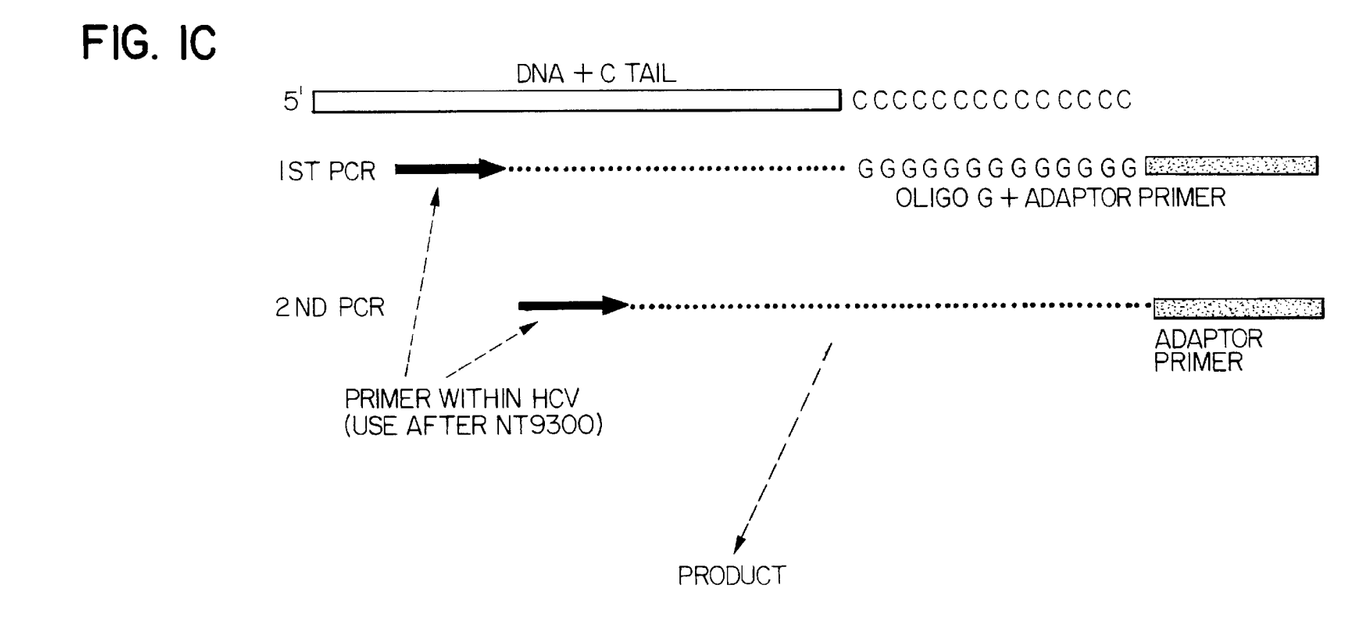

The Anchor PCR Process allows the PCR primer to have a suitable sequence different from the template sequence and carries out PCR as schematically shown in FIG. 1C. In this case, the anchor was added further to the 3'-end than the poly C tail added to the 3'-end of cDNA of the said HCV. This anchor was designed to have a sequence containing the recognition sequence of restriction enzyme located more on the 5' side than poly G which is complementary to poly C tail in the synthesized complementary chain. As a second PCR product, a sequence combining oligo C and adaptor at the end of HCV genome 3'-end is obtained.

1) First-stage PCR

The following reaction liquid was prepared in a microtube: 2.0 μl of the "ten-fold concentration buffer," 1.6 μl of dNTP (2.5 mM each), 1.6 μl of the "primer 2" (10 μM), 1.6 μl of the "primer 3" (10 μM), 4.0 μl of dC tail added cDNA and 8.9 μl of water. Now, the "Primer 2" corresponds to HCV-JT base 9348–9367/5'-GGCATCTACCTGCTCCCCAA-3' (SEQ ID NO: 6), while the "Primer 3" is 5'-TGCTGTCGACTACTCGAGCAGGG GGGGGGGGGGGGGG-3' (SEQ ID NO: 7) containing poly G sequence complementary to poly C tail and XhoI recognition sequence (CTCGAG). The composition of the "ten-fold concentration buffer" is 0.7M Tris-HCl (pH 8.8), 0.3M KCl, 0.1M ammonium sulfate, 20 mM $MgCl_2$, 10 mMDTT, 1 mg/ml bovine serum albumin, and 1.0% Triton X-100.

To this reaction liquid, one drop of mineral oil was added to pile up, and after heating for 2 minutes at 98° C., it was held at 82° C., to which 0.3 μl of Taq polymerase (available for Angewandte Gentechnologie Systeme GmbH) were added. Thereafter, a cycle of 93° C. for 40 seconds, 55° C. for 45 seconds, and 72° C. for 2 minutes was repeated 34 times, thereby allowing PCR to take place.

2) Second-stage PCR

The following reaction liquid was prepared in a microtube: 5.0 μl of the "ten-fold concentration buffer," 4.0 μl of dNTP (2.5mM each), 4.0 μl of the "primer 4" (10 μM), 4.0 μl of the "primer 5" (10 μM), 2.5 μl of the first PCR reaction liquid and 29.8 μl of water. Now, the "Primer 4" corresponds to HCV-JT base 9363–9382, and in addition, XhoI recognition sequence was added, and has 5'-GCGTAATCTCGAGCCCAACCG GTGAACCGGGAG-3' (SEQ ID NO:8). The "Primer 5" is the same sequence as 20 residual base on the 5'-side of the "Primer 3" and has 5'TGCTGTCGACTACTCGAGCA-3' (SEQ ID NO:9). The composition of the ten-fold concentration buffer" has the same composition as that of the first-step PCR. To this reaction liquid, two drops of mineral oil were added to pile up, and after heating for 2 minutes at 98° C., it was held at 82° C., to which 0.7 μl of Taq polymerase (available from Angewandte Gentechnologie Systeme GmbH) were added. Thereafter, by the reaction cycle same as that of the first-step PCR, PCR was allowed to take place. After treating the reactant with phenol/chloroform, ethanol precipitation was carried out and the precipitant residue was dissolved in 10 μl of water.

[Example 6] Subcloning

Because the primers used for the above second-stage PCR all contain the recognition sequence of restriction enzyme XhoI, for the product aimed by the above second-stage PCR, the recognition sequence of XhoI are synthesized on both sides at two places. Consequently, if these were digested with XhoI, fragments with the broken terminal of XhoI on both ends are generated, one end of which has its broken terminal located outside the 3'-end of HCV. The 3'-end of HCV was cloned by integrating this fragment into the vector digested with XhoI in the same manner.

Digestion by restriction enzyme XhoI was carried out by reacting 40 μl of the product of the said second-stage PCR for 2 hours at 37° C. After digestion, the reaction liquid was phenol/chloroform-treated and ethanol precipitation was allowed to take place. Thereafter, agarose electrophoresis was carried out on XhoI digested DNA, the size of the DNA fragment was confirmed by ethidium bromide staining, and DNA having a size greater than about 100 base pairs were adsorbed in the DEAE cellulose paper. The cellulose paper with DNA adsorbed was heated for 20 minutes at 65° C. in the elusion buffer [1M NaCl, 0.1 mN EDTA, Tris-HCl (pH 8.0)] to elute DNA, and this DNA eluent was phenol/chloroform-treated and was subject to ethanol precipitation. The precipitate residue was dissolved in 10 μl of water and XhoI fragments were recovered.

BluescriptKS+ (available from Toyobo Company), a vector holding the ampicillin resistant gene, was digested with XhoI, dephosphatized by alkaline phosphotase (derived from calf small intestine) treatment, and the XhoI-digested vector was prepared. This XhoI-digested vector was mixed with the above XhoI fragment recovered solution, and using a ligation kit (available from Takara Shuzo Company), and the mixture was reaction for 1 hour at 16° C. to insert the PCR fragment into the vector. Using this reaction liquid, *Escherichia coli* competent cell JM109 (available from Takara Shuzo Company) was transformed, and the bacteria liquid was applied to the ampicillin plate.

[Example 7] Screening

First of all, a clone to which an HCV-JT fragment was inserted by colony hybridization was chosen. The ampicillin resistant colony was transferred to a nitrocellulose filter, and DNA was denatured by the 0.5N NaOH and 1.5M NaCl solutions and neutralized with 1M Tris-HCl (pH 7.4), and then, depressurized and dried for 3 hours at 80° C. Oligomer DNA (5'-AGCTAGGGCACTCCAGGCC AATAGGCCATCCCC-3': SEQ ID NO: 10) which corresponds to base 9381–9412 of HCV-JT and is 5'-end-labeled with $^{32}$P was used for a probe, and hybridization reaction was allowed to take place for 24 hours at 40° C. in a reaction liquid (50 mM sodium phosphate buffer (pH 7.4), 0.9M NaCl, 5 mM EDTA, 0.1% bovine serum albumin, 0.1% Ficoll, 0.1% polyvinyl pyrrolidone, 0.1% SDS, and 0.1 mg/ml denatured salmon sperm DNA). Then, the filter was washed with 2×SSC, 0.1% SDS (twice for 10 minutes at room temperature), and further with 1×SSC, 0.1% SDS (twice for 30 minutes at 55° C.), and a positive (having an insert of HCV-JT fragment) colony was detected by autoradiography.

As a result of colony hybridization, of clones judged to be positive, clones having a longer insert were detected by PCR. "Primer 5" and "Primer 6" comprising 5'-AAACACTCCAGGCCAATAGG-3' (corresponding to base 9385–9404 of HCV-JT; SEQ ID NO: 11) were used as primers. A reaction liquid [1.0 μl of the ten-fold concentration buffer (above-mentioned), 0.8 μl of dNTP (2.5 mM each), 0.8 μl of "Primer 5" (10 μM), 0.8 μl of "Primer 6" (10 μM), and 6.3 μl of water] was prepared in a microtube, to which part of the positive colony was suspended. Under the conditions same as those of anchor PCR (first-stage PCR) of Example 5. PCR was allowed to take place. The reaction products were subject to electrophoresis and the insert length was confirmed.

[Example 8] Sequence Determination

Plasmid of a clone having a comparatively long insert was prepared, and the sequence of the insert was determined by the dideoxy method. using a sequencing kit (Sequenase Ver 2, available from USB Company). As a result, "Sequence 3'X" Table 1/SEQ ID NO: 1), which has not yet been known in the HCV-JT sequence was obtained. The length of sequence was 98 bp. In addition, between the U stretch and "Sequence 3'X" a "transition area" was newly found.

In "Sequence 3'X," a special stem and loop structure predicted from the secondary structure of RNA exited.

[Example 9] Analysis of Clinical Sample

Based on the "Sequence 3'X" obtained in this experiment, any sign of existence of sequence was checked in clinical samples by RT-PCR and Southern blot technique. FIG. 3 shows the position of the primer and probe used.

RNA was prepared by the clinical samples (liver or serum). For RNA from liver, operation same as that carried out in Example 1 and 2 was carried out. For RNA of serum derivation, after the serum was diluted with the equal amount of water and RNA was recovered with "Isogen LS Reagent" (Nippon Gene Company), RNA was subject to ethanol precipitation and was dissolved in water.

From these RNAs (1 μg/μl) prepared by the liver or serum, reverse transcription reaction was carried out in the same manner as operations in Example 3, using "Primer 7" (see FIG. 3 Table 2; 5'-ACATGATCTGCAGAGAGG CC-3'; SEQ ID NO: 12) and cDNA was synthesized. Then, the following first-stage PCR was allowed to take place. 3.0 μl of the above-mentioned "ten-fold concentration buffer," 2.4 μl dNTP (2.5 mM each), 2.4 μl of "Primer 7" (10 μM), 2.4 μl of "Primer 8" (see FIG. 3; 5'-TTTCCTTCTTTGGTGGCTCC-3'; SEQ ID NO: 13) (10 μM), 1.5 μl of the above-mentioned cDNA and 17.9 μl of water were mixed. To this reaction liquid, one drop of mineral oil was added, and after heating for 2 minutes at 98° C., it was held at 82° C., to which 0.45 μl of Taq polymerase (available from Angewandte Gentechnologie Systeme GmbH) were added. Thereafter, by the cycle of 93° C. for 40 seconds, 55° C. for 45 seconds, and 72° C. for 2 minutes was repeated 34 times.

TABLE 1

Conventional 3' untranslated area ————————> |<———————————— U stretch which was regarded as 3' terminus previously

CUAAACACUCCAGGCCAAUAGGCCAUCCCUUUUUUUUUGUUUUUUUUUUUUCUUUUUUUUUUUUUCUUUUUUUUUU
9383

——————————————————————————————>|<——Transitional region——>|<————   3'X   ——·
UUUUUUUUUUUUCUUCUUUGUUUUUUUUUUUUCCCUUUUUCCUUCUUUGGUGGCUCCAUCUUAGCCCUAGUCACGGC
                                                                                              1                                                                            > |

UAGCUGUGAAAGGUCCGUGAGCCGCAUGACUGCAGAGAGUGCUGAUACUGGCCUCUCUGCAGAUCAUGU
                                                                                                                                                                98

U stretch includes a small number of C as well as G and A.
Slight variations are observed in the length of U stretch with a single sample. (30–100 bp)
We temporarily name a region, where C appears frequently at the end of U stretch, as transition area. Transition area shows many different patterns within a single sample.

TABLE 2

The position and the direction of each primer in "Sequence 3X"
R3 is a probe for southern blotting Successively, the following second-stage PCR was carried out. 5.0 µl of the above-mentioned "ten-fold concentration buffer," 4.0 µl dNTP (2.5 mM each), 4.0 µl of "Primer 9" (see Table 2; 5'-CCATCTTAGCCCTAGTCAC G-3'; SEQ ID NO: 14) (10 µM), 4.0 µl of "Primer 10" (see Table 2; 5'-TCAGCACTCTCTGCAGTCAT-3'; SEQ ID NO: 15) (10 µM), 2.0 µl of the above-mentioned cDNA and 30.3 µl of water were mixed. To this reaction liquid, two drops of mineral oil were added to pile up, and after heating for 2 minutes at 98° C., it was held at 82° C., to which 0.7 µl of Taq polymerase (available from Angewandte Gentechnologie Systeme GmbH) were added. Thereafter, by the cycle of 93° C. for 40 seconds, 55° C. for 45 seconds, and 72° C. for 2 minutes was repeated 34 times. The size of reaction product was confirmed by agarose electrophoresis using 10 µl of reaction product, and a clone having the desired 67-bp size was detected.

Some clones detected by size confirmation of final products or by electrophoresis were verified by the Southern blot technique. The reaction products were divided by agarose electrophoresis and this was transferred by a capillary transfer technique to the positive charge nylon membrane (HybondN+, available Amersham Company) with 0.4N NaOH. Then, the membrane was neutralized with 1M Tris-HCl (pH 7.4) and then incubated for 1 hour at 50° C. in a reaction liquid (50 mM sodium phosphate buffer (pH 7.4), 0.9M NaCl, 5 mM EDTA, 0.1% bovine serum albumin, 0.1% Ficoll, 0.1% polyvinyl pyrrolidone, 0.1% SDS, and 0.1 mg/mL denatured salmon sperm DNA). Then, $10^6$ cpm/ml of the probe R3 (oligomer corresponding to 5'CGGCTCACGGACCTTTCACA-3' has the end labeled with $^{32}$P; SEQ ID NO: 16) were added and was allowed to undergo hybridization reaction for 24 hours at 50° C. Then, the filter was washed with 2×SSC, 0.1% SDS (twice for 10 minutes at room temperature), and further with 1×SSC, 0.1% SDS (twice for 30 minutes at 55° C.), and by autoradiography using an image analyzer (BAS3000, available from Fuji Film Company), presence of "Sequence 3'X" was analyzed. As a result, examples in which the existence of "Sequence 3'X" include 4 cases in 4 samples of HCV infected liver (type II/1b), 0 case in 3 samples of HCV noninfected liver, 19 cases in 23 samples of HCV-infected serum (typing was not done). 2 cases in 2 samples of HCV-infected serum (III/2a type), 0 case in 11 samples of HCV-infected serum, and 0 case in 10 samples of normal serum. As described above, in HCV-infected sample, "Sequence 3'X" exists in high frequency. In the analysis using II/1b type and III/2a type serums, "Sequence 3'X" was detected in both serum types. Because by the analysis using the liver and serum, "Sequence 3'X" was detected specifically for HCV infection, it has been indicated that this sequence is useful for inspection to confirm HCV infection.

[Example 10] Analysis of "3'X Sequence" of II/1b type HCV

Cloning of "Sequence 3'X" of II/1b type HCV in the HCV infected serum sample and determination of its base sequence were carried out by the RTPCR technique same as that in Example 9. In this event, the area from the known 3'-end area to the 3'X area through the poly U tail was divided in two areas overlapping each other for carrying out RT-PCR. For the first area (inside of Sequence 3'X), the said primer 7 was used as a primer for reverse transcription reaction, and in the first-stage PCR, "Primer 7" and "Primer 11" (see Table 2; 5'-CTTTGGTGGCTCCATCTTAG-3'; SEQ ID NO: 17) were used, and in the second-stage PCR, "Primer 12" (see FIG. 3; sequence with XhoI site added to Primer 7; 5'-CACGATCACTCGAGACA TGATCTGCAGAGAGGCC-3'; SEQ ID NO: 18) and "Primer 13" (see Table 2; sequence with the XhoI site added; 5'-AGTAATGCCTCGAGTGGCTCCAT CTTAGCCCTA-3'; SEQ ID NO: 19) were used.

For the second area (area with poly U tail held between), "Primer 10" stated in Example 9 was used for the primer for reverse transcription and in the first-stage PCR, "Primer 2" stated in Example 5 and "Primer 14" (see FIG. 3; 5'-CTGCAGTCATG CGGCTCACG-3'; SEQ ID NO: 20) and in the second-stage PCR, "Primer 4" and "Primer 15" (see Table 2; sequence with the XhoI site added; 5'-CGCGATAACTCGAGCACGGACCTTTCACAGCTAG 3'; SEQ ID NO: 21) were used.

Subcloning was carried out on the second-stage PCR products in the first and the second areas (about 120 base pairs and 200 base pairs, respectively) in the same manner as in the case of Example 6. When the base sequence was determined in the same manner as in the case of Example 8 with respect to the liver-derived II/1b type clone (21 clones derived from 4 samples) obtained in Example 8 and serum-derived II/1b type clone (22 clones derived from 4 samples) obtained in the present Example, there existed clones with variation in the base with the bases stated below in the sequence of Table 3. Specifically, A at the 25-position varied to G, G at the 28-position to A, C at the 54-position to T, T at the 60-position to C, A at the 63-position to G, A at the 65-position to G, and C at the 71-position to T. "SEQ ID NO: 1" containing the said variation is stated as "SEQ ID NO: 2." It has been determined that compared to other areas, "Sequence 3'X" is an area with less variations between clones of II/1b type.

TABLE 3

```
                    1            10           20           30           40           50           60
From U stretch  ... GGTGGCTCCA  TCTTAGCCCT  AGTCACGGCT  AGCTGTGAAA  GGTCCGTGAG  CCGCATGACT
                                                 G    A                              T       C
                   70           80           90           98
                GCAGAGAGTG  CTGATACTGG  CCTCTCTGCA  GATCATGT
                   G  G          T
```

[Example 11] Determination of Base Sequence of "Sequence 3'X" of III/2a Type HCV The sequence of the 3'X area of serum HCV III/2a type was determined by the RT-PCR technique of the second area in the similar manner to that of Example 10. The position and the direction of each primer in "Sequence 3'X" shown in Table 2. The overall sequence was determined by synthesizing the sequences of two overlapping areas. With respect to the first area (inside of sequence 3'X), all the operations were carried out in the manner identical to those in Example 10. With respect to the second area (area with poly U tail put in-between), for the primer of reverse transcription reaction, "Primer 10" was used, and at the first-stage PCR, "Primer 14" and "Primer 16" (sequence corresponding to base 9356–9375 of HC-J6 (Okamoto et al. J. Gen. Virol. 72, 2697–2704, 1991) which is III/2a type HCV; 5'-GTGTCGCGTGCCCGACCCCG-3'; SEQ ID NO: 22) was used for the second-stage PCR, "Primer 15" and "Primer 17" (sequence with the XhoI site added to the sequence corresponding to the position of base 9380–9399 of HC-J6; 5'-GTAATGTCTCGAGTTACTCCT TGGCCTACTCCT-3'; SEQ ID NO: 23) were used.

Subcloning was carried out on a DNA fragment of about 120 bp for the first area and a DNA fragment of about 300 bp or 200 bp for the second area in the same manner as in the case of Example 6 and the base sequence was determined in the same manner as in the case of Example 8. As a result, "Sequence 3'X"(Table 4; SEQ ID NO: 3) nearly same as that of HCV II/1b was obtained. The sequence length was 98 bp and only 72-position was different as compared to HV II/1b. (U in the II/1b type was C in the III/2a type.) Same as HCV II/1b type, a "transition area" was observed between the U stretch and "Sequence 3'X." This transition area has a sequence characteristic to the III/2a type. By the way, in Table 4 or SEQ ID NO: 3, the sequence from the 3'-end to 20 bp "5'-GGCCUCUCUGCAGAUCAUGU-3'" is the sequence derived from "Primer 7" used for cloning but considering that "Primer 7" specifically hybridized the III/2a type genome and PCR reaction progressed, there is a high possibility that the III/2a type genome possesses the same sequence. (It is evident that the objectives of this invention such as detection of the III/2a type, etc. can be achieved by at least using this sequence.)

detected in the base with the base stated below in the sequence of Table 4. In the inside of "Sequence 3'X," specifically, U at 43-position varied to C and G at 66-position varied to C. There existed a mutant with C at 61-position deletion. With respect to serum-derived III/2a type HCV, 15 clones (5 clones each from 3 samples) were analyzed for the area 1 and 10 clones (5 clones each from 2 samples) for the area 2, and the results shown in Table 4 were obtained.

Furthermore, there existed another mutant with UA on 74 and 75 position instead of AU and with U on 81 position instead of C. The sequence of "SEQ ID NO: 3" containing the said all mutants above described is stated as "SEQ ID NO: 4."

Based on the above results, it has been clarified that "Sequence 3'X" has well conserved sequences in the II/1b type and III/2a type and is an area with less variation between clones of the III/2a type.

This invention has clarified the base sequence of the 3'-end which is highly conserved in HCV and is assumed to be important for multiplication and highly reliable HCV detection and development of effective HCV inhibitors have become possible.

TABLE 4

Conventional NS58 area                              Conventional 3' untranslated area ——————>|<——

ACUUUCCGUAGGGGUAGGCCUCUUUUUACUCCCCGCUCGGUAGAGCGGCACACAUUAGCUACACUCCAUAGCUAACUG UUUUUCUUUUUUU
G     U    CGA    CG      U   CC            Termination codon    G      U U stretch                           ——>|<——            Transitional region          ——>|<——

UUUUUUUUUUUU UUUUUUUUUUUUUUUUUUUUUUU UUUUUUUU CUUUCUUUUCUUUUCUC ACCUUACUUUACUUCCUUUCUUGGUGGCUCC
                                                                                       C  U   U        C 1
                                    Area in which mutation is frequent
                            Sequence 3'X                    ——————————————————>

AUCUUAGCCCUAGUCACGGCUAGCUGUGA AAGGUCCGUGAGCCGCAUGACU GCAGAGAGUGCCGAUACUGGCCUCUCUGCAGAUCAUGU
                         C                       #          C                                    98

III/2a type, existence of A in the transition are is a characteristics.
Sequence 3'X with 98 bp length has nearly same sequence as that of II/1b.
There existed a clone on #-position missing.

When the sequence of "Sequence 3'X" of the III/2a type clone was determined from serum 2 sample, mutation was

What is claimed is:

1. An isolated single-stranded nucleic acid which specifically hybridizes a minimum sequence length of 15 nucleotides of a sequence of Sequence ID No: 2 or a sequence complementary to said sequence.

2. The nucleic acid according to claim 1, wherein the minimum sequence length is about 20 nucleotides.

3. An isolated double-stranded nucleic acid according to claim 1, comprising the nucleic acid and its complementary chain.

4. The nucleic acid according to claim 3, wherein the minimum sequence length is about 20 nucleotides.

5. An isolated single-stranded nucleic acid which specifically hybridizes a minimum sequence length of 15 nucleotides of a sequence of SEQ ID NO: 4 or a sequence complementary to said sequence.

6. The nucleic acid according to claim 5, wherein the minimum sequence length is about 20 nucleotides.

7. An isolated double-stranded nucleic acid according to claim 5, comprising the nucleic acid and its complementary chain.

8. The nucleic acid according to claim 7, wherein the minimum sequence length is about 20 nucleotides.

9. A primer comprising the DNA of claim 1 or 5.

10. A kit for detecting C-type hepatitis virus containing the primer according to claim 9.

11. A primer comprising the DNA of claims 2 or 6.

12. A kit for detecting C-type hepatitis virus containing the primer according to claim 11.

13. A process for detecting C-type hepatitis virus, comprising carrying out PCR for a sample using the primer according to claim 9.

14. A process for detecting C-type hepatitis virus, comprising carrying out PCR for a sample using the primer according to claim 11.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear     ( i i ) MOLECULE TYPE: RNA (genomic)

( x i ) SEQUENCE DESCRIPTION: SEQ ID NO:1:

```
GGUGGCUCCA UCUUAGCCCU AGUCACGGCU AGCUGUGAAA GGUCCGUGAG CCGCAUGACU    60
GCAGAGAGUG CUGAUACUGG CCUCUCUGCA GAUCAUGU                            98
```

( 2 ) INFORMATION FOR SEQ ID NO:2:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear     ( i i ) MOLECULE TYPE: RNA (genomic)

( x i ) SEQUENCE DESCRIPTION: SEQ ID NO:2:

```
GGUGGCUCCA UCUUAGCCCU AGUCACGGCU AGCUGUGAAA GGUCCGUGAG CCGCAUGACY    60
GCAGAGAGUG CUGAUACUGG CCUCUCUGCA GAUCAUGU                            98
```

( 2 ) INFORMATION FOR SEQ ID NO:3:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear     ( i i ) MOLECULE TYPE: RNA (genomic)

( x i ) SEQUENCE DESCRIPTION: SEQ ID NO:3:

```
GGUGGCUCCA UCUUAGCCCU AGUCACGGCU AGCUGUGAAA GGUCCGUGAG CCGCAUGACU    60
GCAGAGAGUG CCGAUACUGG CCUCUCUGCA GAUCAUGU                            98
```

( 2 ) INFORMATION FOR SEQ ID NO:4:

( i ) SEQUENCE CHARACTERISTICS:
        ( A ) LENGTH: 98 base pairs
        ( B ) TYPE: nucleic acid
        ( C ) STRANDEDNESS: single
        ( D ) TOPOLOGY: linear     ( i i ) MOLECULE TYPE: RNA (genomic)

( x i ) SEQUENCE DESCRIPTION: SEQ ID NO:4:

```
GGUGGCUCCA UCUUAGCCCU AGUCACGGCU AGCUGUGAAA GGYCCGUGAG CCGCAUGACU    60
GCAGASAGUG CCGWWACUGG YCUCUCUGCA GAUCAUGU                            98
```

( 2 ) INFORMATION FOR SEQ ID NO:5:

( i ) SEQUENCE CHARACTERISTICS:
        ( A ) LENGTH: 20 base pairs ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "Primer"

( x i ) SEQUENCE DESCRIPTION: SEQ ID NO:5:

TACTCCTACT CTCTGTAGGG 20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "Primer"

( x i ) SEQUENCE DESCRIPTION: SEQ ID NO:6:

GGCATCTACC TGCTCCCCAA 20

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "Primer"

( x i ) SEQUENCE DESCRIPTION: SEQ ID NO:7:

TGCTGTCGAC TACTCGAGCA GGGGGGGGGG GGGGGGGG 38

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "Primer"

( x i ) SEQUENCE DESCRIPTION: SEQ ID NO:8:

GCGTAATCTC GAGCCCAACC GGTGAACGG GAG 33

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
            ( A ) DESCRIPTION: /desc = "Primer"

( x i ) SEQUENCE DESCRIPTION: SEQ ID NO:9:

TGCTGTCGAC TACTCGAGCA 20

( 2 ) INFORMATION FOR SEQ ID NO:10:

( i ) SEQUENCE CHARACTERISTICS:
        ( A ) LENGTH: 32 base pairs ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "Primer"

( x i ) SEQUENCE DESCRIPTION: SEQ ID NO:10:

AGCTAAACAC TCCAGGCCAA TAGGCCATCC CC 32

( 2 ) INFORMATION FOR SEQ ID NO:11:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "Primer"

( x i ) SEQUENCE DESCRIPTION: SEQ ID NO:11:

AAACACTCCA GGCCAATAGG 20

( 2 ) INFORMATION FOR SEQ ID NO:12:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "Primer"

( x i ) SEQUENCE DESCRIPTION: SEQ ID NO:12:

ACATGATCTG CAGAGAGGCC 20

( 2 ) INFORMATION FOR SEQ ID NO:13:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "Primer"

( x i ) SEQUENCE DESCRIPTION: SEQ ID NO:13:

TTTCCTTCTT TGGTGGCTCC 20

( 2 ) INFORMATION FOR SEQ ID NO:14:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: other nucleic acid
                ( A ) DESCRIPTION: /desc = "Primer"

( x i ) SEQUENCE DESCRIPTION: SEQ ID NO:14:

CCATCTTAGC CCTAGTCACG 20

( 2 ) INFORMATION FOR SEQ ID NO:15:

( i ) SEQUENCE CHARACTERISTICS:
                ( A ) LENGTH: 20 base pairs ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:15:

TCAGCACTCT CTGCAGTCAT 20

( 2 ) INFORMATION FOR SEQ ID NO:16:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:16:

CGGCTCACGG ACCTTTCACA 20

( 2 ) INFORMATION FOR SEQ ID NO:17:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:17:

CTTTGGTGGC TCCATCTTAG 20

( 2 ) INFORMATION FOR SEQ ID NO:18:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:18:

CACGATCACT CGAGACATGA TCTGCAGAGA GGCC 34

( 2 ) INFORMATION FOR SEQ ID NO:19:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Primer"

( x i ) SEQUENCE DESCRIPTION: SEQ ID NO:19:

AGTAATGCCT CGAGTGGCTC CATCTTAGCC CTA 33

( 2 ) INFORMATION FOR SEQ ID NO:20:

( i ) SEQUENCE CHARACTERISTICS:
( A ) LENGTH: 20 base pairs (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:20:

CTGCAGTCAT GCGGCTCACG                                                                        20

(2) INFORMATION FOR SEQ ID NO:21:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:21:

CGCGATAACT CGAGCACGGA CCTTTCACAG CTAG                                                        34

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:22:

GTGTCGCGTG CCCGACCCCG                                                                        20

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:23:

GTAATGTCTC GAGTTACTCC TTGGCCTACT CCT                                                         33

(2) INFORMATION FOR SEQ ID NO:24:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Adaptor Primer"

(x i) SEQUENCE DESCRIPTION: SEQ ID NO:24:

CCCCCCCCCC CCCC                                                                              14

(2) INFORMATION FOR SEQ ID NO:25:

(i) SEQUENCE CHARACTERISTICS:
        (A) LENGTH: 13 base pairs ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Adaptor Primer"

( x i ) SEQUENCE DESCRIPTION: SEQ ID NO:25:

GGGGGGGGGG GGG                                                                                          13

( 2 ) INFORMATION FOR SEQ ID NO:26:

( i ) SEQUENCE CHARACTERISTICS:
( A ) LENGTH: 224 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:26:

CUAAACACUC CAGGCCAAUA GGCCAUCCCU UUUUUUUGU UUUUUUUUU UUCUUUUUUU             60

UUUUUUCUUU UUUUUUUUUU UUUUUUUUUU CUUCUUUGUU UUUUUUUUUU CCCUUUUUCC         120

UUCUUUGGUG GCUCCAUCUU AGCCCAGUC ACGGCUAGCU GUGAAAGGUC CGUGAGCCGC          180

AUGACUGCAG AGAGUGCUGA UACUGGCCUC UCUGCAGAUC AUGU                                       224

( 2 ) INFORMATION FOR SEQ ID NO:27:

( i ) SEQUENCE CHARACTERISTICS:
( A ) LENGTH: 119 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:27:

TTTTTTCCCT TTCCTTCTT TGGTGGCTCC ATCTTAGCCC TAGTCACGGC TAGCTGTGAA            60

AGGTCCGTGA GCCGCATGAC TGCAGAGAGT GCTGATACTG GCCTCTCTGC AGATCATGT          119

( 2 ) INFORMATION FOR SEQ ID NO:28:

( i ) SEQUENCE CHARACTERISTICS:
( A ) LENGTH: 98 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

GGTGGCTCCA TCTTAGCCCT AGTCACGGCT AGCTGTGAAA GGTCCGTGAG CCGCATGACT           60

GCAGAGAGTG CTGATACTGG CCTCTCTGCA GATCATGT                                                        98

( 2 ) INFORMATION FOR SEQ ID NO:29:

( i ) SEQUENCE CHARACTERISTICS:
( A ) LENGTH: 271 base pairs
( B ) TYPE: nucleic acid
( C ) STRANDEDNESS: single
( D ) TOPOLOGY: linear ( i i ) MOLECULE TYPE: RNA (genomic)

( x i ) SEQUENCE DESCRIPTION: SEQ ID NO:29:

ACUUUCCGUA GGGGUAGGCC UCUUUUUACU CCCCGCUCGG UAGAGCGGCA CACAUUAGCU            60

-continued

| | | | | | | |
|---|---|---|---|---|---|---|
| ACACUCCAUA | GCUAACUGUU | UUUCUUUUUU | UUUUUUUUUU | UUUUUUUUUU | UUUUUUUUUU | 120 |
| UUUUUUUUUU | UUUUCUUUCU | UUUCUUUUCU | CACCUUACUU | UACUUCCUUU | CUUGGUGGCU | 180 |
| CCAUCUUAGC | CCUAGUCACG | GCUAGCUGUG | AAAGGUCCGU | GAGCCGCAUG | ACUGCAGAGA | 240 |
| GUGCCGAUAC | UGGCCUCUCU | GCAGAUCAUG | U | | | 271 |